United States Patent [19]

Della Valle et al.

[11] Patent Number: 5,567,716
[45] Date of Patent: Oct. 22, 1996

[54] TRANS AND CIS TRAUMATIC ACID SALTS HAVING CICATRIZANT ACTIVITY ASSOCIATED TO BACTERIOSTATIC, ANTIVIRAL, ANTIBIOTIC OR ANTIFUNGAL ACTIVITY

[75] Inventors: Francesco Della Valle; Silvana Lorenzi, both of Padova; Gabriele Marcolongo, Carrara San Giorgio, all of Italy

[73] Assignee: Lifegroup S.p.A., Rome, Italy

[21] Appl. No.: 155,153

[22] Filed: Nov. 19, 1993

[30] Foreign Application Priority Data

Nov. 23, 1992 [IT] Italy ................. MI92A2674

[51] Int. Cl.$^6$ ................. A61K 31/195; A61K 31/20
[52] U.S. Cl. ................. 514/332; 534/676; 534/773; 544/242; 548/161; 548/164; 548/310.1; 548/341.5; 546/105; 546/267; 546/347; 564/205; 514/150; 514/256; 514/297; 514/358; 514/368; 514/394; 514/397; 514/460; 514/494; 514/495; 514/547
[58] Field of Search ................. 546/347, 267, 546/105; 514/358, 494, 495, 150, 297, 256, 332, 367, 368, 394, 397, 460, 547; 544/242; 534/676, 773; 548/161, 164, 310.1, 341.5; 564/205

[56] References Cited

U.S. PATENT DOCUMENTS

| | | | |
|---|---|---|---|
| 3,542,826 | 11/1970 | Pacini | 514/501 |
| 3,720,773 | 3/1973 | Pacini | 514/501 |
| 3,808,314 | 4/1974 | Pacini | 514/501 |

OTHER PUBLICATIONS

Chemical Abstracts, vol. 108, No. 25, Abstract No. 230587z, p. 600, Jun. 20, 1988.
Chemical Abstracts, vol. 105, No. 17, Abstract No. 163, 456d, p. 712, Oct. 27, 1986.
Chemical Abstracts, vol. 83, No. 3, Abstract No. 29,1165, p. 40, Jul. 21, 1975.
Nakayama et al, *Bull Chem. Soc. Jpn.* vol. 64, pp. 358–365 (1991).
Breslow et al, *J. Am. Chem. Soc.*, vol. 103 (10) pp. 2905–2907 (1981).
Zimmerman et al, Plant Physiol. (1979) 63, 536–541, "Identification of Traumatin, A Wound Hormone, as 12–oxo–Trans–10 Dodecenoic Acid".
English et al, J. Biol. Chem. vol.121, No. 2, (1937), 791–799, "The Wound Hormones of Plants: I. Traumatin, the Active Principle of the Bean Test".
Goldemberg, J. Soc. Cosmet. Chem., 28, (Nov. 1977), 667–679, "Reduction of Topical Irritation".
Miyamoto et al, J. Soc. Cosmet, Chem. Japan, vol. 22, No. 4, (1989), 254–262, "Effects of Cosmetics Containing Bioactive Substances on Skin".
Rodriguez–Bigas et al, Plastic and Reconstructive Surgery, vol. 81, No. 3 (Mar. 1988), 386–389, "Comparative Evaluation of Aloe Vera in the Management of Burn Wounds in Guinea Pigs".
Phytomorphology, vol. 25, No. 3, 1975, pp. 265–261 (sic), B. G. L. Swamy et al, "Wound Healing Responses in Monocotyledons—II. Responses to Chemical Treatments".

*Primary Examiner*—Zinna Northington Davis
*Attorney, Agent, or Firm*—Watson Cole Stevens Davis, P.L.L.C.

[57] ABSTRACT

Traumatic acid salts, wherein B is a cation selected from:
  a) a quaternary ammonium,
  b) a cation of a linear or branched $C_1$–$C_{20}$ mono-, di- or trialkanolamine,
  c) a cation of a biologically active primary, secondary or tertiary amine,
  d) silver or zinc cation,
and relative pharmaceutical compositions administrable by topical or parenteral route For the therapeutic treatment of cutaneous pathologies in which it is important to associate an a bacteriostatic, antibiotic, antifungal or an antiviral activity, to the cicatrizant effect, typical of traumatic acid.

10 Claims, No Drawings

TRANS AND CIS TRAUMATIC ACID SALTS HAVING CICATRIZANT ACTIVITY ASSOCIATED TO BACTERIOSTATIC, ANTIVIRAL, ANTIBIOTIC OR ANTIFUNGAL ACTIVITY

FIELD OF THE INVENTION

The present invention relates to traumatic acid salts for the treatment of cutaneous pathologies where it is important to associate a bacteriostatic, antibiotic, antifungal or an antiviral activity, to the cicatrizant effect, typical of traumatic acid.

PRIOR ART

In spite of its thinness, skin plays a key role in the protection of the human organism from the external environment, in fact life is not possible when a large area of the skin mantle is seriously damaged, as in the case of various burns.

This global role of protection acts in different ways which, individually considered, represent as many skin functions.

Skin offers a remarkable resistance to traction, not only thanks to horny layer cells interdigitation and to the presence of an abundant collagen filling in dermis, but also thanks to the peculiar organization of the fibrous structure containing the elastic tissue. Thanks to these characteristics, skin performs a mechanical protection against traumatic insults and a function of a two way barrier. In fact it allows the dispersion of water (perspiratio insensibilis) and of catabolism products that are secreted by glands and conversely hampers the penetration of chemical substances, microorganisms of radiations present in the environment. Moreover skin plays a key role in maintaining both the thermal and pressor homeostasis and has functions of deposit and synthesis. Finally skin has two very important characteristics namely, the sensorial function, as it is the center of pselaphesia and of the immunological sensitivity, since it is the immunocompetent cells center.

Cutaneous integrity maintenance allows therefore to conserve unchanged the above mentioned physiological functions. Traditional medicine has recognized over the centuries numerous plants used in the form of extracts or decoctions able to aid the healing of wounds.

Still now aloe infusions and decoctions are used because of their antiphlogistic, astringent and cicatrizant effect in the treatment of burns while Asian centella and tricticum vulgaris extracts are still used for the preparation of pharmaceutical products used for the cicatrization (M. Rodriguez-Bigas et al., Comparative Evaluation of Aloe Vera in the Management of Burn Wounds in Guinea Pigs, Plastic and Reconstructive Surgery, 1988).

In the last years a growing interest has been developed in the attempt to isolate and to identify the substances responsible For the pharmacological effect with the aim to understanding the difficult pharmacology of the vegetal extracts.

Traumatic acid owing its name to its property to repair damages in the vegetal tissue has been indicated as the active principle in the tricticum vulgaris extract and in the aloe vera infusion and as such it was the object of numerous patents. (Pacini, U.S. Pat. No. 3,720,773, "Cobaltous trans-traumatate for topical treatment of herpetic keratitis"). Chemically speaking traumatic acid or 10-dodecendioic is a linear long chain dicarboxylic acid having 12 carbon atoms and an unsaturated bond: the anti-irritant activity of the traumatic acid seems to be due to the carboxylic group distribution along the carbon chain (R. L. Goldemberg et al., Reduction of topical irritation, J. Chem. Soc. , 28, 667–679. 1977). Traumatic acid identification was described for the first time by English and Bonnernel (The Wound Hormones of Plants, The Journal of Biological Chemistry, vol. 121, No.2, 1937), is a vegetable hormone specifically produced by several plants as the reaction to the damage of their tissues and it is able to induce the cellular proliferation and differentiation necessary to heal wound and to create the physiological stimulus for the healing of continuous solutions.

Traumatic acid is formed in plants by oxidation of linoleic acid to 3-peroxylinoleic acid, which is subsequently transformed into the Final product by enzymatic route thanks to the action of hydroperoxy-lyase (Zimmerman D. C., C. A. Condron, Identification of Traumatin, a Wound Hormone, as 12-Oxo-trans-10-dodecenoic Acid, Plant Physiol. 63,536–541, 1979).

The same ability to heal wounds has been recognized in the experimental animal wherein the trans-traumatic acid demonstrated (when administered by topical route) a reepithelializing and antiirritant action and furthermore showing effectiveness on an in vivo herpetic keratitis model both after topic and systemic administration.

(I. Miyamoto et al., Effects of cosmetics containing bioactive substances on skin, J. Soc. Cosmet. Chem. Japan, Vol. 22, No.4 1989).

These pharmacological effects were subsequently reconfirmed in man, where traumatic acid is proposed for burns therapy since it reduces the reepithelialization times, probably increasing the hydration layer of the cutaneous tissue, promoting cohesion between keratinocytes, reducing the edematous condition since it promotes the water transepidermic passage, and finally increasing the cells metabolism in the lesion area.

Positive clinical results were also observed in psoriatic patients or in patients affected by acne, dermatitis seborrheic, neurodermatitis and itches of various origin but also by diseases of vital origin as for example trachoma, herpetic keratitis, verruca (Pacini 1973). With reference to the above mentioned pathologies, it is important to rely on a drug that together with the cicatrizant and lenitive activities has an antiseptic and/or antibacterial activity and therefore broadening the traumatic acid action pattern.

THE PRESENT INVENTION

The applicant has unexpectedly found that trans and cis traumatic acid salts of formulae (I) and (II)

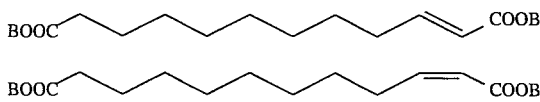

wherein B is a biologically active cation as defined in one of the following classes:

a) a quaternary ammonium cations of respectively general formula (III) and (IV)

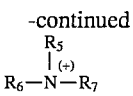

wherein $R_1$, $R_2$, $R_3$ and $R_4$ are equal or different from each other and are selected from:

i) a linear or branched alkyl radical having from 1 to 20 carbon atoms optionally containing in the aliphatic chain at least one of the following groups: arylenoxy, alkylenoxy, and being optionally substituted in the aliphatic chain with at least one of the following residues: aryl, aryloxy and alkoxy groups;

ii) a cycloalkyl radical of from 3 to 10 carbon atoms;
$R_5$ and $R_6$ in formula (IV) form with the nitrogen atoms of the amine a pyridine ring, $R_7$ is a $C_1$–$C_{20}$ linear or branched alkyl radical, b) is a cation of a $C_1$–$C_{20}$ linear or branched mono-, di- or trialkanolamine, c) a cation of a biologically active primary, secondary or tertiary amine having a biological activity as defined in one of the following activities:
 i') disinfectant, antiseptic and bacteriostatic activity,
 ii') antibiotic activity,
 iii') antiviral activity,
 iv') antifungal activity, d) is a cation of a metal selected From silver and zinc, not only retain the peculiar capacity of the traumatic acid or of the considered cation, but these characteristics are associated and enhanced.

These specific properties are to be considered of special interest because many antiseptic substances when topically used do not facilitate but often inhibit wound healing. The present invention refers to their use in the preparation of pharmaceutical compositions for the therapeutic treatment of cutaneous pathologies wherein to the cicatrizant and lenitive effect it is important to associate a bacteriostatic, antibiotic, antiviral or antifungal activity.

DETAILED DESCRIPTION OF THE INVENTION

The characteristics and the advantages of the traumatic acid salts of the present invention are better explained in the following detailed description.

The obtained therapeutic activities render these compounds considerably interesting in the treatment of the traumatic cutaneous injuries where it is important to promote the reepithelialization: wounds and infected wounds but also acne, dermatitis seborrheic, neurodermatitis, itches of various origin, psoriasis and diseases of vital origin as for example trachoma, herpetic keratitis, verrucae. In addition to the therapy for these clear pathologies we have also to hypothesize on the base of clinical observations relating to the "hydrating" effect of the traumatic acid, the utilization of these derivatives in those situations of curls reduced autosterilizing capacity by hydrolipidic film alteration and reduced resistance to the mechanical insults caused by the reduced tissues elasticity. When B in the traumatic acid salts of general formula (I) is a quaternary ammonium cation it is preferably selected from the following ones: hexadecyltrimethylamonium, dodecyltrimethylamonium and octyl-trimethylamonium or a mixture thereof, i.e. cetrimide, benzyldimethylhexadecylammonium, benzyldimethyldodecylammonium and benzyldimethyloctylammonium or a mixture thereof, namely benzethonium, methylbenzethonium, cetylpyridinium, cetyldimethylammonium, dodecyldimethyl (2-phenoxyethyl)-ammonium, hexadecyl(2-hydroxychlorohexyl) dimethyl-ammonium.

All these quaternary ammonium cations have antiseptic and disinfectant property, the same property can also be found for the silver and zinc cations.

When B is the cation coming from an amine as defined in class (b) it is preferably selected from the group consisting of ethanolamine and 2-propanolamine, diethanolanime and di-2-propanolamine.

The biologically active amines belonging to class (c) subclass i' ) are namely those having disinfectant, antiseptic and bacteriostatic activity, and selected from the group consisting of chlorhexidine, mafenide, hexamethylpararosaniline, aminacrine, ethoxazene and phenazopyridine. Some of these amines such as ethoxazene and phenazopyridine may also have analgesic and/or antiinflammatory activity. The biologically active amines of class c) subclass ii'), having antibiotic activity are selected from the group consisting of amikacin, gentamicin, kanamycin, bekanamycin, neomycin, streptomycin tobramycin, lincomycin, clindamycin, erythromycin, colistin, polymyxin B, tetracycline, chlorotetracycline, rolitetracycline, oxytetracycline, spectinomycin, viomycin, bacampicyline, or stallimycin (A Distamycine).

A biologically active amine of class c) subclass iii'), having antiviral activity are is Tromantadine.

The biologically active amines of class c) subclass iv') are selected from the group consisting of: miconazole, econazole. chlormiconazole, chlormidazole, isoconazole, bifonazole, diamthazole, halethazole, hexetidine.

The following examples are reported for illustrative but not limitative purposes.

EXAMPLE 1

Preparation of hexadecyltrimethylammonium trans-traumatate 2.28 g (10 mmol) of trans-traumatic acid are suspended in 50 ml of water cooled to 4 ° C. 7.3 g (20 mmol) of a hexadecyltrimethylamonium bromide solution in 100 ml of water is eluted in a column cooled to 4 ° C. and containing 35 ml of an anionic exchange resin Dowex 1×8 generated in the OH⁻form. The eluate free from bromide anions is recovered in the form of traumatic acid suspension maintained under stirring at 4 ° C. The resulting solution is frozen and lyophilized.

7.7 g of pure product are obtained.

The physical chemical characteristics of hexadecyltrimethyl-ammonium trans-traumatate are the following:

physical state: white powder
raw formula: $C_{50}H_{102}N_2O_4$
molecular weight: 795.38
elemental analysis: C=75.50%; H=12.93%; N=3.52%; O=8.05% (calculated)
C=75.20%; H=13.11%; N=3.47%; O=8.22% (found)
solubility in org. solv.:>20 mg/ml in ethanol
solubility in water:>10 mg/ml
TLC: eluent chloroform/methanol/$H_2O$/28% $NH_3$ 50:40:7:3
Rf=0.67 (traumatic acid)
Rf=0.18 (cetrimide).

EXAMPLE 2

Preparation of benzylmethylhexadecylammonium trans-traumatate.

2.28 g (10 mmol) of trans-traumatic acid are suspended in 50 ml of water cooled to 4 °C.

8.28 g (20 mmol) of a benzylmethylhexadecylammonium chloride solution in 90 ml of water and 10 ml ethanol are eluted in a column cooled to 4 °C. and containing 35 ml of an anionic exchange resin Dowex 1×8 generated in the OH⁻ form. The eluate free from chloride anions is recovered in the form of a traumatic acid suspension maintained under stirring at 4 °C. The resulting solution is frozen and lyophilized.

9.2 g of pure product are obtained.

The physical chemical characteristics of the benzylmethylhexadecylammonium trans-traumatate thus obtained are the following:

physical state: amorphous white deliquescent powder raw formula: $C_{62}H_{110}N_2O_4$ molecular weight: 947.58 elemental analysis: C=78.59%; H=11.70%; N=2.96%; O=6.75% (calculated): C=78.30%; H=11.81%; N=2.89%; O=6.81% (found)

solubility in org. solv.: >20 mg/ml in ethanol solubility in water: >10 mg/ml

TLC: eluent:chloroform/methanol/$H_2O$/28% $NH_3$ 50:40:7:3 Rf=0.67 (traumatic acid) RF=0.6.3 (benzyldimethyl-hexadecyl-ammonium).

EXAMPLE 3

Preparation of silver trans-traumatate 2.28 g of trans-traumatic acid (10 mmol) are suspended in 20 ml water at 4° C., neutralized using NaOH 1N, sheltered from light. The resulting suspension, kept at 4° C., is exposed to a nitrogen stream and a solution of 3.4 g $AgNO_3$ in 20 ml water is slowly added drop by drop under continuous stirring.

The resulting precipitate is separated by filtration, washed three times using 10 ml of cool water and finally dried under high vacuum. The reaction yield is 4.1 g of dry product.

The physical chemical properties of silver trans-traumatate are the following:

physical state: white amorphous powder raw formula: $C_{12}H_{18}O_4Ag_2$ molecular weight: 442,02 elemental analysis: C=32.61%; H=4.10%; O=14.48%; Ag=48.81%. (calculated): C=32.29%; H=4.21%; O=14.82%; Ag=48.68%. (found)

traumatic acid 51.65% (as free acid)

water solubility: poorly soluble (>10 mg/ml in 5% NH3)

organic solvent solubility: poorly soluble in DMSO and ethanol

TLC: eluent chloroform/methanol/water/28% $NH_3$ 50:40:7:3; Rf=0.67 (traumatic acid)

EXAMPLE 4

Preparation of zinc trans-traumatate 2.28 g of trans-traumatic acid (10 mmol) are suspended in 20 ml cool water at 4° C. and neutralized using NaOH 1N.

A solution of 2.88 g $ZnSO_4$ eptahydrate (10 mmol) in 20 ml water is slowly added drop by drop to the resulting solution, kept at 4° C. and under continuous stirring.

The resulting mixture is heated to 40° C. for 3 hours and then cooled to 4° C. for further 15 hours.

The precipitate is recovered by filtration, washed three times using 10 ml of cool water and finally dried under high vacuum.

The reaction yield is 2.65 g of dry product.

The physical chemical properties of Zinc trans-traumateate are the following:

physical state: white amorphous powder raw formula: $C_{12}H_{18}O_4Zn$ molecular weight: 291,67 elemental analysis: C=49.42%; H=6.22%; O=21.94%; Zn=22.42% (calculated): C=49.11%; H=6.23%; O=21.82%; Zn=22.84%, (found)

traumatic acid: 78,27% (as free acid)

water solubility: poorly soluble (>10 mg/ml in 5% $NH_3$)

organic solvent solubility: poorly soluble in DMSO and ethanol

TLC: eluent chloroform/methanol/water/28% $NH_3$ 50:40:7:3; Rf=0.67 (traumatic acid)

EXAMPLE 5

Preparation of benzethonium trans-traumatate 2,28 g of trans-traumatic acid (10 mmol) are suspended in 50 ml of water cooled to 4° C.

A solution of 9,0 g of Benzethonium chloride (20 mmol) in 90 ml of water is eluted through a column cooled to 4° C. and containing 35 ml of [OH—] Dowex 1×8 resin.

The eluate free from chlorides is then frozen and lyophilized. The reaction yield is 10.5 g of dry product.

The physical chemical properties of benzethonium trans-traumatate are the following:

physical state: deliquescent solid raw formula: $C_{66}H_{102}N_2O_8$ molecular weight: 1051.56 elemental analysis: C=75.39%; H=9.78%; N=2.66%; O=12.17%; (calculated):

C=75.31%; H=9.84%; N=2.58%; O=12.27%; (found)

traumatic acid: 21.71% benzethonium: 85.23% (as benzethonium chloride)

water solubility: >10 mg/ml organic solvent solubility: >10 mg/ml in ethanol

TLC: eluent chloroform/methanol/water/28% $NH_3$ 50:40:7:3; Rf=0.67 (traumatic acid): eluent ethanol/water/acetic acid 70:20:10; Rf=0.53 (benzethonium)

EXAMPLE 6

Preparation of tobramycin trans-traumatate 11.4 g of trans-traumatic traumatic acid (50 mmol) are suspended in 200 ml of cool water at 4° C., A solution of 14.3 g of tobramycin sulfate (20mmol) in 200 ml of water is eluted through a column cooled to 4° C. containing 150 ml of [OH—] Dowex 1×8 resin. The eluate free from sulfate is collected into the suspension of traumatic acid kept under continuous stirring at 4° C. The resulting solution is frozen and lyophilized.

The reaction yield is 20.2 g of dry product,

The physical chemical properties of tobramycin trans-traumatate are the following:

physical state: white amorphous powder raw formula: $C_{96}H_{174}N_{10}O_{38}$ molecular weight: 2076.5 elemental analysis: C=55.53%; H=8.45%; N=6.75%; O=29.28%; (calculated): C=55.26%; H=8.68%; N=6.96%; O=29.10%; (found)

traumatic acid: 54.97% (as free acid)

tobramycin: 68.64% (as tobramycin sulfate)

water solubility: >10 mg/ml organic solvent solubility: >10 mg/ml in DMSO

TLC: eluent chloroform/methanol/water/28% $NH_3$ 50:40:7:3; Rf=0.67 (traumatic acid): eluent chloroform/methanol/28% $NH_3$ 50:40:10; Rf=0.05 (tobramycin)

EXAMPLE 7

Preparation of gentamycin trans-traumatate 11.4 g of trans-traumatic acid (50 mmol) are suspended in 200 ml of water cooled to 4° C.

A solution of 14.4 g gentamycin sulfate (20 mmol) in 200 ml of water are eluted through a column cooled at 4° C. and containing 150 ml [OH—] Dowex 1×8 resin. The eluate free from sulfate is collected in the form of a traumatic acid suspension kept under continuous stirring at 4° C. The resulting solution is frozen and lyophilized. The reaction yield is 20.6 g of dry product.

The physical chemical properties of gentamycin trans-traumatate are the following:

physical state: white amorphous powder raw formula: $C_{102}H_{186}N_{10}O_{34}$ molecular weight: 2096,7 elemental analysis: C=58.43%; H=8.94%; N=6.68%; O=25.95%; (calculated): C=58.21%; H=9.05%; N=6.59%; O=26.17%; (found)

traumatic acid: 54.44% (as free acid)

gentamycin: 68.975 (as gentamycin C1 sulfate)

water solubility: >10 mg/ml organic solvent solubility: >10 mg/ml in DMSO

TLC: eluent chloroform/methanol/water/28% $NH_3$ 50:40:7:3; RF=0.67 (traumatic acid): eluent chloroform,/methanol/28% $NH_3$ 1:1:1 ninhydrin as indicator: three stains are observed like in gentamycin sulfate used as standard sample.

EXAMPLE 8

Preparation of lincomycin trans-traumatate 2.28 g of trans-traumatic acid (10 mmol) are suspended in 100 ml of water cooled to 4° C. A solution of 8.86 g of lincomycin hydrochloride (20 mmol) in 100 ml water is eluted through a column cooled to 4° C. containing 35 ml of [OH—] Dowex 1×8 resin. The eluate free from chlorides is collected in the form of a suspension of traumatic acid kept under continuous stirring at 4° C. The resulting solution is frozen and lyophilized. The reaction yield is 10.1 g of dry product.

The physical chemical properties of lincomycin trans-traumatate are the following:

physical state: white amorphous powder raw formula: $C_{48}H_{88}N_4O_{16}S_2$ molecular weight: 1041,38 elemental analysis: C=55.36%: H=8.52%; N=5.38%: O=24.58%: S=6.16% (calculated): C=54.98%; H=8.69%; N=5.31%; O=25.015 S=6.01 (found)

traumatic acid: 21.92% (as free acid)

lincomycin: 85.08% (as lincomycin hydrochloride)

water solubility: >10 mg/ml organic solvent solubility: >10 mg/ml in DMSO

TLC: eluent chloroform/methanol/water/28% $NH_3$ 50:40:7:3; Rf=0.67 (traumatic acid): eluent ethanol/water/acetic acid 70:20:10 Rf=0.61 (lincomycin)

EXAMPLE 9

Preparation of Erythromycin trans-traumatate 2.28 g of trans-traumatic acid (10 mmol) are suspended in 100 ml of water/ethanol 2:1 mixture at 4° C. 14.7 g of erythromycin free base (20 mmol) are added and the resulting mixture is kept under stirring at 4° C. for 3 hours and then heated to 25° C. overnight. 200 ml water ape then added. The mixture is concentrated under vacuum to a volume of about 100 ml and cooled to 4° C.

The resulting precipitate is recovered by filtration, washed three times using 10 ml of cool water and finally dried under high vacuum. The reaction yield is 16.3 g of dry product.

The physical chemical properties of erythromycin trans-traumatate are the following:

physical state: white amorphous powder raw formula: $C_{86}H_{154}N_2O_{30}$ molecular weight: 1696.19 elemental analysis: C=60.90%; H=9.15%; N=1.65%; O=28.3%; (calculated): C=60.60%; H=9.32%; N=1.58%; O=28.5%; (found)

traumatic acid: 13.46% (as free acid)

erythromycin: 86.54% (as free base)

water solubility: poorly soluble organic solvent solubility: >10 mg/ml in DMSO and ethanol TLC: eluent chloroform/methanol/water/28% $NH_3$ 50:40:7:3; RF=0.67 (traumatic acid): eluent chloroform/methanol/water/28% $NH_3$ 80:25:2:1; Rf=0.86 (erythromycin)

EXAMPLE 10

Preparation of rolitetracycline trans-traumatate 2.28 g of trans-traumatic acid (10 mmol) are suspended in 200 ml of water at 4° C. under nitrogen stream and sheltered From light. A solution of 10.6 g rolitetracycline (20 mmol) in 100 ml $H_2O$ is slowly added drop by drop in 30 minutes to the above suspension The resulting mixture is frozen and lyophilized.

The reaction yield is 12.6 g of dry product.

The physical chemical properties of rolitetracycline transtraumarate are the following:

physical state: amorphous yellow-brown powder raw formula: $C_{66}H_{86}N_6O_{20}$ molecular weight: 1283.5 elemental analysis: C=61.77%; H=6.75%; N=6.55%; O=24.93%; (calculated): C=61.62%; H=6.90%; N=6.49%; O=24.99%; (found)

traumatic acid 17.79% (as free acid)

rolitetracycline 82.21% (as free base)

water solubility >10 mg/ml organic solvent solubility: >10 mg/ml in DMSO

TLC: eluent chloroform/methanol/water/28% $NH_3$ 50:40:7:3; Rf=0.67 (traumatic acid): eluent butanol/acetic acid/water 4:2:2; Rf=0.53 (rolitetracycline)

EXAMPLE 11

Preparation of chlorhexidine trans-traumatate 2,28 g of trans-traumatic acid (10 mmol) are suspended in 100 ml of a mixture water/ethanol 2: 1 at 4° C., 5,05 g of chlorhexidine base (10 mmol) are added and the mixture is kept under stirring at 4° C. for hours and then at 25° C.

overnight. 200 ml of water are added and the mixture is concentrated under vacuum at the volume of about 100 ml and Finally again cooled to 4° C. The resulting precipitate is recovered by filtration, washed three times using 10 ml of cool water and finally dried under high vacuum.

The reaction yield is 6.8 g of dry product.

The physical chemical properties of chlorhexidine trans-traumatate are the following:

physical state: white amorphous powder raw formula: $C_{34}H_{50}N_{10}O_4Cl_2$ molecular weight: 733.75 elemental analysis: C=55.66%; H=6.87; N=19.09%; O=8.72%; Cl=9.66% (calculated): C=55.38%; H=6.99%; N=18.92%; O=8.96% Cl=9.75% (found)

traumatic acid: 31.11% (as free acid)

chlorhexidine: 68.98% (as free base)

water solubility: poorly soluble organic solvent solubility: >10 mg/ml in DMSO

TLC: eluent chloroform/methanol/water/28% $NH_3$ 50:40:7:3; Rf=0.67 (traumatic acid): eluent chloroform/methanol/28% $NH_3$ 50:40:10 Rf=0.77 (chlorhexidine)

EXAMPLE 12

Preparation of ethanolamine trans-traumatate 2.28 g of trans-traumatic acid (10 mmol) are suspended in 100 ml of water at 4° C. A solution of 1.23 g ethanolamine as free base in 20 ml water, under continuous stirring is slowly added drop by drop in 30 minutes to the resulting suspension.

The resulting mixture is frozen and lyophilized.

The reaction yield is 3.5 g of dry product.

The physical chemical properties of ethanolamine trans-traumatate are the following:

physical state: white amorphous powder raw formula: $C_{16}H_{34}N_2O_6$ molecular weight: 350.46 elemental analysis: C=54.84%; H=9.78%; N=7.99%; O=27.39%; (calculated): C=54.58%; H=9.84%; N=8.02%; O=27.62%; (found)

traumatic acid: 65.14% (as free acid)

ethanolamine: 34.86% (as free base)

water solubility: >10mg/ml organic solvent solubility: >10 mg/ml in ethanol

TLC: eluent chloroform/methanol/water 28% $NH_3$ 50:40:7:3; Rf=0.67 (traumatic acid)

EXAMPLE 13

Preparation of miconazole trans-traumatate 9.58 g of miconazole nitrate (20 mmol) are suspended in 300 ml of water and 5 ml of 30% $NH_4OH$ are added. The resulting mixture is extracted 3 times using each time 100 ml of chloroform and the organic phases ape washed 3 times with 50 ml of water, submitted to anhydrous condition using $Na_2SO_4$ and then collected together and evaporated under vacuum.

2.28 g of trans-traumatic acid (10 mmol) are added to the raw residue solubilized in 200 ml of ethanol. The resulting mixture is evaporated under vacuum and the residue dried under high vacuum, The reaction yield is 20.5 g of dry product.

The physical chemical properties of miconazole trans-traumatate physical state: white amorphous powder raw formula: $C_{48}H_{48}N_4O_6Cl_8$ molecular weight: 1060.6 elemental analysis: C=54.36%; H=4.56%; N=5.28%; O=9.05%; Cl=26.74 % (calculated): C=54 52%; H=4.61%, 61%; N=5.17%; Cl=26.50% (found)

traumatic acid: 78.47% (as free acid)

ethanolamine: 21.53% (as free base)

water solubility: >10 mg/ml organic solvent solubility: >10 mg/ml in ethanol

TLC: eluent chloroform/methanol/water/28% $NH_3$ 50:40: 7: 3; RF=0. 67 (traumatic acid): eluent chloroform/methanol/water/28% $NH_3$ 80:25:2:1; Rf=0.93 (miconazole)

BIOLOGICAL ACTIVITY

For purposes of clarity the product tested in the following pharmacological trials are those prepared as described in the above reported chemical preparations examples. Therefore they are all salts of trans-traumatic acid.

These trials have the aim to evaluate both the cicatrizant activity of these compounds with respect to that of traumatic acid and the antibacterial activity with respect to a comparison molecule having the same activity in suitable trials carried out in vitro.

1. Effect of cellular proliferation evaluated on fibroblasts of the traumatic acid salts.

Experiments on 3T3 fibroblasts 1.1a Materials and methods.

Cells preparation

Mice 3T3 fibroblasts cultures sown at a 40.000/ml concentration on plates having 6 wells in a DMEM culture medium enriched with 10% calf serum are used. After 24 hours culture, the 90 prepared wells are divided in order to allow the analyses of the compounds of the invention, every compound to be tested being used respectively at a concentration of 0.1, 1 and 10 µg/ml by subsequent evaluations after 48 and 72 hours of incubation.

Compounds solubilization:

Hexadecyltrimethylammoniun (ETA) traumatare: solubilized in water and brought to the desired final concentrations of 0.1. 1 and 10 µg/ml by progressive dilutions;

Ethanolamine traumatate: solubilized in water and brought to the final concentrations of 0.1, 1 and 10 µg/ml by progressive dilutions;

Traumatic acid: neutralized with sodium hydroxyde and solubilized in water, then brought to the final concentrations of 0.1, 1 and 10 µg/ml by progressive dilutions with the culture medium.

The compounds are added to the cells after 24 hours culture. The cells number is measured by colorimetry with the neutral red intravital stain after 24, 48, 72 hours of incubation.

Results:

These compounds act according to a dose—effect relation. Particularly hexadecyltrimethylammonium (ETA) traumatare, ethanolamine traumatare, and traumatic acid at 0.1 µg/ml concentration are able to affect cells proliferation according to a not statistically significant trend. At the concentration of 1 µg/ml hexadecyltrimethylammonium (ETA) traumarate>ethanolamine traumatare=traumatic acid are able to increase cellular proliferation. At the highest concentration (10 µg/ml) the compounds tend to reduce or at least not to increase cellular proliferation. From a biological standpoint the compounds give more significant results after 48 hour (table 1.1-a), although already after 24 hours a higher effect is observed if compared to that obtained with control cultures. A side control experiment is also carried out in which the cultures confluence is evaluated: the cultures treated with hexadecyltrimethylammonium traumatare and ethanolamine traumatare>traumatic acid reduce the time normally necessary for the cells to reach the confluence.

These data demonstrate that these compounds are able to stimulate cicatrization processes.

1.1b Materials and methods
Cell growth

Mouse Balb/C 3T3 fibroblasts were grown in DMEM medium supplemented with penicillin (100 units/ml) and streptomycin (0.1 mg/ml). For experimental purposes, cells are routinely inoculated in 6.4 μm diameter culture dishes (5000cells/dish) and cultured overnight. After 24 hours the culture medium was decantated and the compounds to be tested are added in the presence of 10% foetal calf serum (FCS).

The cells are incubated at 37° C. in 5% $CO_2$ air for 4 (t0), 24 (t1) and 48 (t2) hours before cell density measurement by colorimetry using crystal violet (exposure for 15 minutes, room temperature, absorbance 570nm).
Compounds solubilization The compounds to be tested are solubilized in DMEM+ 10%FCS and DMSO to obtain the final concentration of $10^{-5}M$, $10^{-6}M$ e $10^{-7}M$ in 0.05% DMSO.
Results The cells number is measured 4, 24 and 48 hours after seeding. The cell growth is evaluated as t2/t1 ratio (%). The results described in table 1.1-b show that lincomycin traumatate>rolitetracycline traumatate>erythromycin traumatate are capable to promote cell growth at all the tested doses and this effect appears more consistent if compared to the corresponding one of the parent compound traumatic acid.

1.2 Mice fibroblast L 929 cell culture
Materials and methods
Cell growth

Mice fibroblast cells L929, clone derived from connective tissue, are suspended in Eagle's MEM with penicillin (100U/ml)—streptomycin (0.1 mg/ml), seeded in culture dishes (10000cells/dish) and cultured overnight. After 24 hours the culture medium was decantated and the tested compounds are added. The cellular density is measured after 4 (t0) and 24 (t1) hours of incubation at 37° C. in 5% $CO_2$ air by colorimetry using crystal violet (exposure for 15 minutes, room temperature; absorbance 570 nm).
Compounds solubilization The compounds Benzethonium traumarate, gentamycin traumarate acid are solubilized in water at the concentration of $10^{-6}M$, $10^{-7}M$ and $10^{-8}M$, while traumatic acid was solubilized in DMSO at the above mentioned concentrations.
Results The cells number is measured at 4 (t0) and 24 (t1) hours from the seeding. The cell growth is evaluated at t1/t0 rate (%). The results described in table 1.2 show that benzethonium traumarate>gentamycin traumarate ape capable to promote cell growth (proliferation) according to dose-effect relationship and this effect is higher than traumatic acid effect. The above experimental data indicate that the salification process can also increase the proliferative effect in comparison with parent compound.

2. Antibacterial activity of the traumatatic acid salts 2.a diffusion method in agar-germs
Materials and methods
Bacterial suspention preparation:

In a Tryprone Soy Agar diffusion medium ATCC (American Type Culture Collection) standard bacterial strains are inoculated, preparing a final solution of $10^6$ cfu/g (colony forming unities) of the following strains:

| | |
|---|---|
| Pseudomonas Aeruginosa | ATCC 35422 |
| Cepacia | ATCC 25416 |
| Maltophilia | ATCC 13637 |
| Staphylococcus Aureus | ATCC 65380 |
| Staphylococcus Epidermidis | ATCC 14990 |
| Streptococcus Fecalis | ATCC 29212 |
| Escherichia Coli | ATCC 35248 |
| Candida Albicans | ATCC 10231 |
| Aspergillus Niger | ATCC 16404 |

Plates preparation

Every plate contains 20 ml of a medium where 2 equidistant wells having a standard diameter are Formed and in each of these wells 200 μg of the above described bacterial solution are inoculated. 2 plates are prepared for every couple of compounds to be tested at different concentrations, and For every strain, and each of these plates is compared with a white (sterile demineralized water inoculum). After the inoculum, the plates are placed in the refrigerator to favour diffusion and temporaneously blocking bacterial growth.

The compounds hexadecyltrimethylammonium traumatate and benzyldimethylhexadecylammonium traumatare respectively versus hexadecyl trimethylammonium bromide and benzyldimethylhexadecylammonium chloride are solubilized in demineralized water to Form solutions at the concentrations: 0.1; 0.5; and 1%.
Parameters The antibacterial effect is evaluated by measuring bacterial diffusion halo around the well vs white (halo absence).
Results The analysis of the results evidences that the two compounds of the invention hexadecyltrimethylammonium traumatare and benzyldimethylhexadecylammonium traumatare have an antibacterial and bacteriostatic activity profile comparable to that of the comparison products hexadecyltrimethylammonium bromide and benzyldimethylhexadecylammonium chloride, indicating that the salification has not altered the original biological properties (Table 2. a).

2.b EVALUATION OF BACTERIOSTATIC MINIMAL CONCENTRATION (BMC)
Materials

1. Culture Medium: Tryprone Soy Broth (TBS) - Biogenetics

2. Saline solution: 0.9 g NaCl in 100 ml demineralized and sterile water

3. Mc Farland solution: 1 ml $BaCl_2$ 1.175% in 99.5 ml 1% $H_2SO_4$

Methods
Bacterial Suspension preparation:

Microbic standard strains from American Type Culture Collection (ATCC) were used, chosen among aerobic Gram positive and negative as follows:

| | |
|---|---|
| Pseudomonas Aeruginosa | ATCC 5422 |
| Safilococcus Aureus | ATCC 5380 |
| Stafilococcus Epidermis | ATCC 14990 |
| Bacillus Subtilis | ATCC 6633 |
| Escherichia Coli | ATCC 35218 |
| Candida Albicans | ATCC 10231 |

The broths culture of the different species are prepared growing the standard strain (kept in Tryptic Soy Agar (TSA) slent at 5° C.) in Tryptone Soy Broth (TSB) for 12 hours at 37° C. 10 ml are then taken up from each culture, centrifugated for 3 times at 3500 PM washing each time the sediment using 10 ml of sterile saline solution. The sediment is resuspended in the saline solution until obtainment of a turbidity corresponding to the Mc Farland standard solution (the suspension title must be $10^{-7}$–$10^{-8}$ UFC/ml).

Preparation of the solutions of the compounds to be tested:

The stock solutions (5% in sterile water, added with 1N HCl in case the salts are poorly soluble in water) of the traumatic acid salts are prepared and kept at 5° C.

Hexadecyltrimethyl ammonium traumatare
Benzyldimethylhexadecyl ammonium traumatare
Zinc traumarate
Silver traumarate
Chlorhexidine traumarate
Benzethonium traumatate
Gentamicin traumatare
Erythromycin traumatare
Tobramycin traumatare
Lincomycin traumatare
Rolitetracycline traumarate The compounds, dissolved as stock solution, were added to test tubes containing 5 ml TBS in order to obtain the desired Final concentration 10000; 5000; 1000; 200; 40; 2; 0.4; 0.05 µg/ml (culture medium maximal dilution=1/10).

Evaluation of Bacteriostatic Minimal Concentration (BMC):

50 µl of bacterial suspension are added to the tube containing the compounds to be tested and incubated at 37° C.: the densitometric determination is made in comparison with Mc Farland standard solution 24 and 48 hours later.

After the incubation time the suspensions ape gently agitated; 50 µl of each suspension are inoculated in tubes containing 5 µl of TSB and incubated at 37° C.; the densitometric determination is made 48 hours later.

BMC is defined by comparison between the two densitometric evaluation.

Results

All the examined compounds show bacteriostatic effect as described in Tables 2.b)1–6. This effect is specific for the different bacterial strains tested. The bacteriostatic effect of each salt is similar to stechiometric concentration of the respective negative ion.

The above experiment suggest that the new salts of traumatic acid here described, capable to promote cell proliferation as shown before, possess also bacteriostatic effect. Furthermore the above experiment show that the salification process does not alter the specific effect that the anion contribute.

TABLE 1.1a

Effects of hexadecyltrimethylammonium (ETA) traumatate and ethanolamine traumatate with respect to traumatic acid on the cellular proliferation of fibroblasts. The cells numeration is accomplished by colorimetric method after 24, 48 and 72 hours of incubation.

| Substance | Concentrations (pg/ml) | | |
|---|---|---|---|
| | 0.1 | 1.0 | 10.0 |
| 24 hours of incubation | | | |
| (Control | 0.579 ± 0.021) | | |
| ETA traumatate | 0.575 ± 0.041 | 0.619 ± 0.033 | 0.491 ± 0.021 |
| ethanolamine traumatate | 0.562 ± 0.013 | 0.609 ± 0.033 | 0.553 ± 0.027 |
| traumatic acid | 0.486 ± 0.029 | 0.510 ± 0.008 | 0.543 ± 0.019 |
| 48 hours of incubation | | | |
| (Control | 1.334 ± 0.050) | | |
| ETA traumatate | 1.553 ± 0.061^ | 1.501 ± 0.081^^ | 0.842 ± 0.078(**) |
| ethanolamine traumatate | 1.415 ± 0.106 | 1.435 ± 0.082^^ | 1.415 ± 0.132^ |
| traumatic acid | 1.497 ± 0.087 | 1.431 ± 0.047^ | 1.442 ± 0.060^ |
| 72 hours of incubation | | | |
| (Control | 2.360 ± 0.125) | | |
| ETA traumatate | 2.501 ± 0.131^^ | 2.503 ± 0.100^^ | 1.385 ± 1.63(**) |
| ethanolamine traumatate | 2.382 ± 0.039^^ | 2.463 ± 0.100^ | 2.408 ± 0.085 |
| traumatic acid | 2.492 ± 0.070^ | 2.349 ± 0.125 | 2.446 ± 0.128 |

Significant increase of neutral red incorporation
^p < 0.5
^^p < 0.01
Significant reduction of neutral red incorporation
*p < 0.5
**p < 0.01

TABLE 1.1b

Effect of lincomycin traumatate, erythromycin traumatate and rolitetracycline traumatate compared to traumatic acid on cell growth in mice 3T3 ribroblast colture

| | Cell density at different time (hours) | | | cell growth |
|---|---|---|---|---|
| | 4(t0) | 24(t1) | 48(t2) | t2/t1 |
| Control | 0.300 +−.045 | 0.481 +−.075 | 0.849 +−.139 | 76.776 +−15.348 |
| Traumatic acid | | | | |
| 10−5M | 0.478 +−.045 | 0.317 +−.074 | 0.657 +−.113 | 112.273 +−17.727 |
| 10−6M | 0.495 +−.096 | 0.320 +−.055 | 0.657 +−.113 | 95.638 +−24.834 |
| 10−7M | 0.459 +−.057 | 0.323 +−.071 | 0.740 +−.097 | 135.554 +−33.092 |
| Lincomycin traumatate | | | | |
| 10−5M | 0.361 +−.049 | 0.228 +−.045 | 0.693 +−.065 | 195.78 +−20.35 |
| 10−6M | 0.352 +−.062 | 0.210 +−.041 | 0.734 +−.127 | 246.29 +−4.87 |
| 10−7M | 0.384 +−.023 | 0.209 +−.069 | 0.705 +−.122 | 247.68 +−58.22 |
| Erythromycin traumatate | | | | |
| 10−5M | 0.370 +−.036 | 0.365 +−.025 | 0.919 +−.107 | 159.16 +−10.42 |
| 10−6M | 0.352 +−.047 | 0.369 +−.027 | 0.921 +−.071 | 148.64 +−4.66 |
| 10−7M | 0.344 +−.055 | 0.368 +−.013 | 1.074 +−.085 | 196.81 +−10.28 |
| Rolitetracycline traumatate | | | | |
| 10−5M | 0.46 +−.074 | 0.255 +−.068 | 0.678 +−.243 | 166.39 +−22.91 |
| 10−6M | 0.475 +−.031 | 0.356 +−.059 | 0.660 +−.170 | 186.69 +−15.13 |
| 10−7M | 0.482 +−.052 | 0.287 +−.102 | 0.828 +−.108 | 185.44 +−44.70 |

TABLE 1.2

Cell growth evaluation in mice ribroblast L929 colture: effect of Benzethonium Traumatate and gentamycin traumatate in comparison with traumatic acid, added at different doses.

| | cell density | | cell growth |
|---|---|---|---|
| | 4h(t0) | 24h(t1) | t1/t0 |
| Control | 0.335 +− .024 | 0.407 +− .040 | 22.4 +− 16.29 |
| Traumatic acid | | | |
| 10−6M | 0.272 +− .028 | 0.404 +− .008 | 50.5 +− 15.18** |
| 10−7M | 0.261 +− .017 | 0.401 +− .039 | 53.63 +− 12.67** |
| 10−8M | 0.327 +− .022 | 0.345 +− .043 | 6.95 +− 19.21 |
| Benzethonium traumatate | | | |
| 10−6M | 0.209 +− .017 | 0.402 +− .024 | 91.06 +− 23.74** |
| 10−7M | 0.266 +− .009 | 0.407 +− .026 | 52.16 +− 11.638 |
| 10−8M | 0.268 +− .014 | 0.363 +− .027 | 35.6 +− 7.57 |
| Gentamycin traumatate | | | |
| 10−6M | 0.251 +− .027 | 0.405 +− .016 | 63.68 +− 17** |
| 10−7M | 0.264 +− .003 | 0.357 +− .019 | 35.3 +− 6.24 |
| 10−8M | 0.299 +− .009 | 0.385 +− .016 | 29 +− 5.03 |

*$p < 0.05$;
**$p < 0.01$

TABLE 2.a

Antibacterial activities of the salts hexadecyltrimethylammonium (ETA) traumatate and benzyldimethylhexadecylammonium (BMA) traumatate respectively versus ETA bromide and BMA chloride.

| | A | | | | | |
|---|---|---|---|---|---|---|
| Concentrations | sol. 1% | | sol. 0.5% | | sol. 0.1% | |
| Tested solutions Standard strains | ETA Traumatate | ETA Bromide | ETA Traumatate | ETA Bromide | ETA Traumatate | ETA Bromide |
| Pseudomonas Aeruginosa ATCC.35422 | n.h. | n.h. | n.h. | n.h. | n.h. | n.h. |
| PS Cepacia ATCC.25416 | 22 | 22 | 19 | 19 | 18 | 18 |
| PS Maltophila ATCC.13637 | 21 | 21 | 15 | 15 | n.h. | n.h. |
| Stafilococcus Aureus ATCC.65380 | 24 | 24 | 24 | 24 | 21 | 21 |
| Stafilococcus Epidermidis ATCC.14990 | 22 | 22 | 22 | 22 | 20 | 20 |
| Streptococcus Fecalis ATCC.291212 | 22 | 22 | 22 | 22 | 20 | 20 |
| E. Coli ATCC.35218 | 15 | 15 | 13 | 13 | n.h. | n.h. |

TABLE 2.a-continued

Antibacterial activities of the salts hexadecyltrimethylammonium (ETA) traumatate and benzyldimethylhexadecylammonium (BMA) traumatate respectively versus ETA bromide and BMA chloride.

| | | | | | | |
|---|---|---|---|---|---|---|
| Candida Albicans ATCC.10231 | 25 | 25 | 24 | 24 | 19 | 19 |
| Aspergillus Niger ATCC 16404 | 22 | 22 | 22 | 22 | 19 | 19 |

B

| Concentrations | sol. 1% | | sol. 0.5% | | sol. 0.1% | |
|---|---|---|---|---|---|---|
| Tested solutions Standard strains | BMA Traumatate | BMA Chloride | BMA Traumatate | BMA Chloride | BMA Traumatate | BMA Chloride |
| Pseudomonas Aeruginosa ATCC.35422 | 14 | 14 | 12 | 12 | n.h. | n.h. |
| PS Cepacia ATCC.25416 | 15 | 15 | 15 | 15 | 12 | 12 |
| PS Maltophila ATCC-13637 | 15 | 15 | n.h. | n.h. | n.h. | n.h. |
| Stafilococcus Aureus ATCC.65380 | 22 | 22 | 22 | 22 | 17 | 17 |
| Stafilococcus Epidermidis ATCC.14990 | 19 | 19 | 17 | 18 | 15 | 15 |
| Streptococcus Fecalis ATCC.291212 | 15 | 15 | 14 | 14 | 12 | 12 |
| E. Coli ATCC.35218 | 13 | 13 | n.h. | n.h. | n.h. | n.h. |
| Candida Albicans ATCC.10231 | 16 | 16 | 15 | 15 | 13 | 13 |
| Aspergillus Niger ATCC.16404 | 19 | 19 | 16 | 16 | 12 | 13 | n.h. = no halo

TABLE 2.b)1

*Ps.aeruginosa* ATCC 35422

| COMPOUND | MINIMAL BACTERIAL CONCENTRATION |
|---|---|
| Hexadecyltrimethyl Ammonium Traumatate | >10,000 |
| Benzyldimethylhexadecyl Ammonium Traumatate | 10,000.00 |
| Zinc Traumatate | >10,000 |
| Silver Traumatate | 40.00 |
| Chlorhexidine Traumatate | 40.00 |
| Benzethonium Traumatate | 200.00 |
| Gentamycin Traumatate | 1,000.00 |
| Erythromycin Traumatate | 10,000.00 |
| Tobramycin Traumatate | 5,000 |
| Lincomycin Traumatate | 10,000.00 |
| Rolitecracycline Traumatate | 10,000.00 |
| Control: positive | |

TABLE 2.b)2

St.aureus ATCC 65380

| COMPOUND | MINIMAL BACTERIAL CONCENTRATION |
| --- | --- |
| Hexadecyltrimethyl Ammonium Traumatate | 1,000.00 |
| Benzyldimethylhexadecyl Ammonium Traumatate | 1,000.00 |
| Zinc Traumatate | >10,000 |
| Silver Traumatate | 40.00 |
| Chlorhexidine Traumatate | 8.00 |
| Benzethonium Traumatate | 2.00 |
| Gentamycin Traumatate | 1,000.00 |
| Erythromycin Traumatate | 10,000.00 |
| Tobramycin Traumatate | 1,000.00 |
| Lincomycin Traumatate | 10,000.00 |
| Rolitetracycline Traumatate | 5,000.00 |
| Control: positive | |

TABLE 2.b)3

E.coli ATCC 35218

| COMPOUND | MINIMAL BACTERIAL CONCENTRATION |
| --- | --- |
| Hexadecyltrimethyl Ammonium Traumatate | 200.00 |
| Benzyidimethylhexadecyl Ammonium Traumatate | 200.00 |
| Zinc Traumatate | >10,000 |
| Silver Traumatate | 40.00 |
| Chlorhexidine Traumatate | 8.00 |
| Benzethonium Traumatate | 40.00 |
| Gentamycin Traumatate | 200.00 |
| Erythromycin Traumatate | 10,000.00 |
| Tobramycin Traumatate | 200.00 |
| Lincomycin Traumatate | 10,000.00 |
| Rolitetracycline Traumatate | 1,000.00 |
| Control: positive | |

TABLE 2.b)4

St.epidermidis ATCC 14990

| COMPOUND | MINIMAL BACTERIAL CONCENTRATION |
| --- | --- |
| Hexadecyltrimethyl Ammonium Traumatate | 8.00 |
| Benzyldimethylhexadecyl Ammonium Traumatate | 2.00 |
| Zinc Traumatate | >10,000 |
| Silver Traumatate | 200.00 |
| Chlorhexidine Traumatate | 2.00 |
| Benzethonium Traumatate | 2.00 |
| Gentamycin Traumatate | 200.00 |
| Erythromycin Traumatate | 10.000.00 |
| Tobramycin Traumatate | n.t. |
| Lincomycin Traumatate | 200.00 |
| Rolitetracycline Traumatate | 200.00 |
| Control: positive | |

TABLE 2.b)5

_B.subtilis_ ATCC 6633

| COMPOUND | MINIMAL BACTERIAL CONCENTRATION |
|---|---|
| Hexadecyltrimethyl Ammonium Traumatate | 2.00 |
| Benzydimethylhexadecyl Ammonium Traumatate | 1,000.00 |
| Zinc Traumatate | >10,000 |
| Silver Traumatate | 200.00 |
| Chlorhexidine Traumatate | 2.00 |
| Benzethonium Traumatate | 8.00 |
| Gentamycin Traumatate | 40.00 |
| Erythromycin Traumatate | 1,000.00 |
| Tobramycin Traumatate | n.t. |
| Lincomycin Traumatate | 1,000.00 |
| Rolitetracycline Traumatate | 40.00 |
| Control: positive | |

TABLE 2.b)6

_C.albicans_ ATCC 10231

| COMPOUND | MINIMAL BACTERIAL CONCENTRATION |
|---|---|
| Hexadecyltrimethyl Ammonium Traumatate | 2.00 |
| Benzyidimethylhexadecyl Ammonium Traumatate | 2.00 |
| Zinc Traumatate | >10,000 |
| Silver Traumatate | >10,000 |
| Chlorhexidine Traumatate | 2.00 |
| Benzethonium Traumatate | 2.00 |
| Gentamycin Traumatate | >10,000 |
| Erythromycin Traumatate | >10,000 |
| Tobramycin Traumatate | n.t. |
| Lincomycin Traumatate | 10,000.00 |
| Rolitetracycline Traumatate | 1,000.00 |
| Control: positive | |

Conclusions

The reported results clearly evidence that the compounds of the present invention by salification of traumatic acid are able to determine a specific and considerable cicatrizant activity associated with a marked antibacterial activity.

These effects may be advantageously used in the pathologies wherein it is desirable to associate a stimulation of tissue reparative processes with an antibacterial effect, also considering that many topical antiseptic agents used in surgical practice do not facilitate, but often inhibit injuries healing.(Meyers, Jawetz and Goldfien Farmacologia Medica chap. 58 Ed. Piccin, 1975).

The salts of the present inventions are therefore useful in human therapy fop the treatment of injuries and infected injuries as a consequence of a surgical operation, fistulae, necrotic processes, ulcerodystrophic alterations ( torpid sores, bedsores, burns, fistulous stabs and rhagades) or, anyway, situations requiring the reaction of the process of epithelial neoformation such as acne, dermatitis seborrheic, neurodermatitis, itches also of allergic nature or dermic phenomena of intoxication without excluding affections of vital origin such as trachoma, herpetic keratitis and verrucae. Moreover pathologies are to be added being more simply related to a delayed or altered dermic layer renewal or involving alterations of the cutaneous hydrolipidic layer (e.g. cutaneous ageing, damage by make-up or cosmetics excess).

For these pathologies both the parenteral (vials for intramuscular use) and the topical administration (creams, ointments, gels and solutions) are foreseen.

The necessary dose to perform the therapeutic effect varies depending on the type and seriousness of the damage and on the considered patient (age, concomitant pathologies). A therapeutic dosage is preferable being comprised between 100 and 300 mg/die with periods variable in relation to the type of pathology and anyway not shorter than two weeks.

Reported hereinbelow for illustrative but not limitative purpose are the following examples of therapeutic compositions containing as active principle some traumatic acid salts of formula (I)

EXAMPLE 1

Cream

Every tube contains 100 g cream

| | |
|---|---|
| ETA traumatate | 1.75 g |
| Cetostearyl alcohol | 7.00 g |
| Isopropylmyristate | 7.00 g |
| Liquid paraffin | 7.00 g |
| White beeswax | 3.00 g |
| Glycerol | 3.00 g |
| Cetomacrogol 100 | 2.20 g |
| Perfume test. 34152 (ICSA) | 0.10 g |

-continued

| Butylhydroxytoluene | 0.01 g |
| Purified water | q.s. to 100 g |

EXAMPLE 2

Nebulizer solution
Every bottle contains 10 ml solution:

| ETA traumatate | 175 mg |
| NaCl | 90 mg |
| $Na_2HPO_4$ | 300 mg |
| $NaH_2PO_4$ | 25 mg |
| Purified water | 9410 mg |

EXAMPLE 3

Vaginal cream
Composition for 100 g product

| BMA traumatate | 1.75 g |
| Glycolethylenaminophenol | 12.2 g |
| Propylenglycol | 11.25 g |
| White mineral jelly | 6.5 g |
| Sodium cetyl stearyl sulphate | 2.73 g |
| Cetyl stearyl alcohol | 19.57 g |
| Decyl oleate | 8.5 g |
| Methyl p-hydroxybenzoate | 69 mg |
| Propyl p-hydroxybenzoate | 29 mg |
| Purified water | q.s. to 100 g |

EXAMPLE 4

Douche
Composition for 100 ml product

| ETA traumatate | 17.5 g |
| Perfume | 5 mg |
| Purified water | q.s. to 100 ml |

We claim:

1. A trans and cis traumatic acid salt of formula (I) and (II)

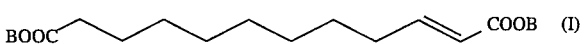 (I)

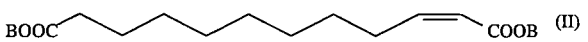 (II)

wherein B is a cation as defined in one of the following classes:

a) quaternary ammonium cations of formulae (III) or (IV)

wherein $R_1$, $R_2$, $R_3$ and $R_4$ are equal or different from each other and are selected from the group consisting of:
  i) a linear or branched alkyl radical having from 1 to 20 carbon atoms optionally containing in the aliphatic chain at least one of the following groups: arylenoxy, alkylenoxy, and being optionally substituted in the aliphatic chain with at least one of the following residues: aryl, arlyoxy and alkoxy groups; and
  ii) a cycloalkyl radical of from 3 to 10 carbon atoms;
  $R_5$ and $R_6$ in formula (IV) form with the nitrogen atom a pyridine ring, $R_7$ is a $C_1$–$C_{20}$ linear or branched alkyl radical;

b) a cation of linear or branched $C_1$–$C_{20}$ mono-, di-, or tri-alkanolamine;

c) a cation of a primary, secondary or tertiary amine belonging to one of the following subclasses:
  i') amines with disinfectant, antiseptic and bacteriostatic activity, selected from the group consisting of chlorhexidine, mafenide, hexamethylpararosaniline, aminacrine, phenazopyridine and ethoxazene;
  ii') amines with antibiotic activity, selected from the group consisting of amikacin, gentamicin, kanamycin, bekanamycin, neomycin, streptomycin, tobramycin, lincomycin, clindamycin, erythromycin, colistin, polymyxin B, tetracycline, chlorotetracycline, rolitetracycline, oxytetracycline, spectinomycin, viomycin, bacampicyline and stallimycin (A Distamycine);
  iii') tromantadine with antiviral activity,
  iv') amines with antifungal activity, selected from the group consisting of miconazole, econazole, chlormiconazole, chlormidazole, isoconazole, bifonazole, diamthazole, halethazole and hexetidine; and d) a cation of a metal selected from silver and zinc.

2. The traumatic acid salt as claimed in claim 1, wherein B is a quaternary ammonium cation selected from the group consisting of: hexadecyltrimethylammonium, dodecyltrimethylammonium and octyltrimethylammonium or a mixture thereof, benzyldimethylhexadecylammonium, benzyldimethyldodecylammonium and benzyldimethyloctylammonium or a mixture thereof; benzethonium, methylbenzethonium, cetylpyridinium, cetyldimethylammonium, dodecyldimethyl (2-phenoxyethyl)-ammonium and hexadecyl(2-hydroxychlorohexyl) dimethyl-ammonium.

3. The traumatic acid salt as claimed in claim 1, wherein, when B is a cation as defined in class (b), it is selected from the group consisting of ethanolamine and 2-propanolamine, diethanolamine and di-2-propanolamine.

4. A therapeutic composition for the therapeutic treatment of cutaneous pathologies when the bacteriostatic, antibiotic, antifungal or antiviral activity is associated to a cicatrizant effect containing as the active ingredient at least one trans and/or cis traumatic acid salt of formula (I) and (II)

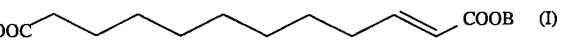 (I)

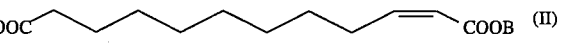 (II)

wherein B is a cation as defined in one of the following classes:

a) quaternary ammonium cations of formulae (III) or (IV)

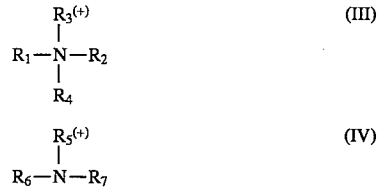

wherein $R_1$, $R_2$, $R_3$ and $R_4$ are equal or different from each other and are selected from the group consisting of:

i) a linear or branched alkyl radical having from 1 to 20 carbon atoms optionally containing in the aliphatic chain at least one of the following groups: arylenoxy, alkylenoxy, and being optionally substituted in the aliphatic chain with at least one of the following residues: aryl, arlyoxy and alkoxy groups; and ii) a cycloalkyl radical of from 3 to 10 carbon atoms; $R_5$ and $R_6$ in formula (IV) form with the nitrogen atom a pyridine ring, $R_7$ is a $C_1$–$C_2$ linear or branched alkyl radical;

b) a cation of linear or branched $C_1$–$C_{20}$ mono-, di-, or tri-alkanolamine;

c) a cation of a primary, secondary or tertiary amine belonging to one of the following subclasses:

i') amines with disinfectant, antiseptic and bacteriostatic activity, selected from the group consisting of chlorhexidine, mafenide, hexamethylpararosaniline, aminacrine, phenazopyridine and ethoxazene;

ii') amines with antibiotic activity, selected from the group consisting of amikacin, gentamicin, kanamycin, bekanamycin, neomycin, streptomycin, tobramycin, lincomycin, clindamycin, erythromycin, colistin, polymyxin B, tetracycline, chlorotetracycline, rolitetracycline, oxytetracycline, spectinomycin, viomycin, bacampicyline and stallimycin (A Distamycine);

iii') tromantadine with antiviral activity, iv') amines with antifungal activity, selected from the group consisting of miconazole, econazole, chlormiconazole, chlormidazole, isoconazole, bifonazole, diamthazole, halethazole and hexetidine; and d) a cation of a metal selected from silver and zinc in combination with suitable excipients and/or diluents.

5. The therapeutic composition as claimed in claim 4 for the treatment of injuries and infected injuries, fistulae, necrotic processes, ulcerodystrophic alterations, acne, dermatitis seborrheic, neurodermatitis, itches, dermic phenomena of intoxication, trachoma, herpetic keratitis and verrucae.

6. The therapeutic composition as claimed in claim 4, wherein B is a quaternary ammonium cation selected from the group consisting of: hexadecyltrimethylammonium, dodecyltrimethylammonium and octyltrimethylammonium or a mixture thereof, benzyldimethylhexadecylammonium, benzyldimethyldodecylammonium and benzyldimethyloctylammonium or a mixture thereof; benzethonium, methylbenzethonium, cetylpyridinium, cetyldimethylammonium, dodecyldimethyl (2-phenoxyethyl)-ammonium, hexadecyl(2-hydroxychlorohexyl) dimethyl-ammonium.

7. The therapeutic composition as claimed in claim 4 wherein, when B is a cation as defined in class (b) it is selected from the group consisting of ethanolamine and 2-propanolamine, diethanolamine and di-2-propanolamine.

8. The therapeutic composition as claimed in claim 4, administrable by parenteral route.

9. The therapeutic composition as claimed in claim 8, wherein the parenteral route is the intramuscular one.

10. The therapeutic composition as claimed in claim 4, administrable by topical route.

* * * * *